US008971603B2

(12) United States Patent
Stancanello

(10) Patent No.: US 8,971,603 B2
(45) Date of Patent: Mar. 3, 2015

(54) METHOD FOR THE FUNCTIONAL VISUALIZATION AND LOCALIZATION OF AN ARTERIOVENOUS MALFORMATION, ROTATABLE IMAGING SYSTEM AND COMBINATION OF A ROTATABLE IMAGING SYSTEM AND AN IRRADIATION UNIT

(75) Inventor: Joseph Stancanello, Gif sur Yvette (FR)

(73) Assignee: Siemens Aktiengesellscahft, München (DE)

( * ) Notice: Subject to any disclaimer, the term of this patent is extended or adjusted under 35 U.S.C. 154(b) by 316 days.

(21) Appl. No.: 13/483,419

(22) Filed: May 30, 2012

(65) Prior Publication Data
US 2012/0308105 A1 Dec. 6, 2012

(30) Foreign Application Priority Data

Jun. 1, 2011 (DE) .......................... 10 2011 076 855

(51) Int. Cl.
| | |
|---|---|
| G06K 9/00 | (2006.01) |
| G01N 23/00 | (2006.01) |
| A61N 5/10 | (2006.01) |
| A61B 6/02 | (2006.01) |
| A61B 6/00 | (2006.01) |
| A61B 6/04 | (2006.01) |
| A61B 19/00 | (2006.01) |

(52) U.S. Cl.
CPC . *A61N 5/10* (2013.01); *A61B 6/025* (2013.01); *A61B 6/481* (2013.01); *A61B 6/486* (2013.01); *A61B 6/504* (2013.01); *A61B 6/5205* (2013.01); *A61B 6/0407* (2013.01); *A61B 6/4085* (2013.01); *A61B 6/4233* (2013.01); *A61B 6/4441* (2013.01); *A61N 2005/1061* (2013.01); *A61B 2019/5238* (2013.01); *A61B 2019/5295* (2013.01)

USPC ............................................. 382/131; 378/19

(58) Field of Classification Search
None
See application file for complete search history.

(56) References Cited

U.S. PATENT DOCUMENTS 5,262,946 A * 11/1993 Heuscher ........................ 378/15
5,588,033 A * 12/1996 Yeung ............................. 378/4

(Continued)

FOREIGN PATENT DOCUMENTS

JP 08206105 A * 8/1996 ............... A61B 6/03
WO WO 2011022336 A2 2/2011

OTHER PUBLICATIONS

H. Schmitt et al.; Reconstruction of blood propagation in three-dimensional rotational X-ray angiography (3D-RA) Schmitt et al.; Computerized Medical Imaging and Graphics, Oct. 2005; vol. 29(7), pp. 507-520, Epub Sep. 2, 2005.; Magazine; 2005.

(Continued)

*Primary Examiner* — Wenpeng Chen

(57) ABSTRACT

A method for functional visualization and localization of an arteriovenous malformation is proposed. A patient is scanned over a predetermined projection angle range during a contrast agent uptake time. The examination region is reconstructed using the projections over the entire projection angle range. The arteriovenous malformation is localized. The multiplicity of the projections is subdivided into at least three partial projection datasets each belonging to different consecutive time windows of the total duration of the scan. A time series having tomosynthesis image datasets is generated by the partial projection datasets. An arterial and/or venous assignment of the vessels flooded with contrast agent takes place based on the time series of tomosynthesis image datasets.

16 Claims, 3 Drawing Sheets

(56) References Cited

U.S. PATENT DOCUMENTS

| | | | |
|---|---|---|---|
| 6,556,697 B1* | 4/2003 | Bruder et al. | 382/131 |
| 6,785,356 B2* | 8/2004 | Grass et al. | 378/4 |
| 6,909,769 B2* | 6/2005 | Bruder et al. | 378/8 |
| 7,532,705 B2* | 5/2009 | Yin et al. | 378/65 |
| 7,953,267 B2* | 5/2011 | Zellerhoff | 382/131 |
| 8,073,224 B2* | 12/2011 | Strobel et al. | 382/130 |
| 8,233,684 B2* | 7/2012 | Licato et al. | 382/128 |
| 8,615,118 B2* | 12/2013 | Yi et al. | 382/128 |
| 2002/0181645 A1* | 12/2002 | Bruder et al. | 378/8 |
| 2003/0013953 A1* | 1/2003 | Mistretta | 600/425 |
| 2003/0040669 A1* | 2/2003 | Grass et al. | 600/407 |
| 2003/0091143 A1* | 5/2003 | Grass et al. | 378/42 |
| 2004/0240604 A1* | 12/2004 | Wang et al. | 378/19 |
| 2005/0015006 A1* | 1/2005 | Mitschke et al. | 600/431 |
| 2005/0152494 A1* | 7/2005 | Katsevich | 378/62 |
| 2006/0115040 A1* | 6/2006 | Chen | 378/19 |
| 2006/0262894 A1* | 11/2006 | Bernhardt et al. | 378/4 |
| 2006/0293579 A1* | 12/2006 | Schmitt et al. | 600/407 |
| 2007/0009080 A1* | 1/2007 | Mistretta | 378/4 |
| 2007/0055148 A1* | 3/2007 | Klingenbeck-Regn | 600/431 |
| 2007/0092055 A1* | 4/2007 | Vives et al. | 378/4 |
| 2007/0230765 A1 | 10/2007 | Wang | |
| 2008/0013675 A1* | 1/2008 | Boese et al. | 378/14 |
| 2008/0024496 A1* | 1/2008 | Deinzer | 345/427 |
| 2008/0031407 A1* | 2/2008 | Satta et al. | 378/15 |
| 2008/0130824 A1* | 6/2008 | Fujisawa | 378/4 |
| 2009/0005668 A1* | 1/2009 | West et al. | 600/407 |
| 2009/0016587 A1* | 1/2009 | Strobel et al. | 382/130 |
| 2010/0128942 A1* | 5/2010 | Licato et al. | 382/128 |
| 2010/0246916 A1* | 9/2010 | Deuerling-Zheng et al. | 382/131 |
| 2011/0038517 A1* | 2/2011 | Mistretta et al. | 382/128 |
| 2014/0037046 A1* | 2/2014 | Grass et al. | 378/8 |

OTHER PUBLICATIONS

Carlo Cavedon et al.: Three-dimensional rotational angiography (3DRA) adds substantial information to radiosurgery treatment planning of AVM's compared to angio-CT and angio-MR, Med. Phys. Aug. 31, 2004(8):2181-2; Others; 2004.

Özkan Özsarlak et al: "MR angiography of the intracranial vessels: technical aspects and clinical applications", Neuroradiology, Dec. 2004 46(12): p. 955-72; Others; 2004.

Frederico Colombo et al.: "Early results of CyberKnife radiosurgery for arteriovenous malformations", J. Neurosurg. Oct. 2009; 111(4):807-19; Others; 2009.

Robert M. Starke et al.: "A comprehensive review of radiosurgery for cerebral arteriovenous malformations: outcomes, predictive factors and grading scales", Stereotact Funct Neurosurg. 2008; 86(3):191-9; Others; 2008.

Xiao et al.; "Treatment of giant cerebral arteriovenous malformation: hypofractionated stereotactic radiation as the first stage", Neurosurgery, Nov. 2010; 67(5):1253-9; Others; 2010.

Chernin et al.: "Digital subtraction arteriography", Curr. Probl. Diagn. Radiol. Nov.-Dec. 1984, 13 (6), p. 1-56; Others; 1984.

Communication from German Patent Office dated Mar. 14, 2012, 11 pages.

* cited by examiner

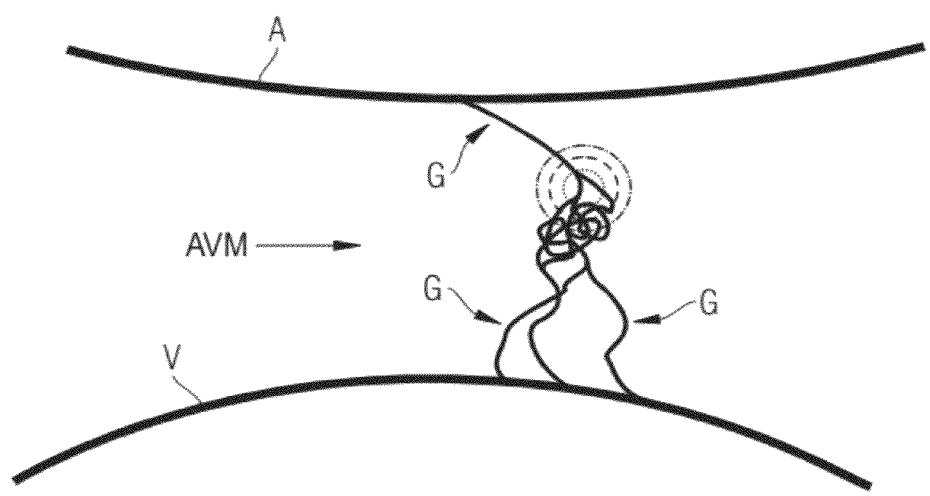

METHOD FOR THE FUNCTIONAL VISUALIZATION AND LOCALIZATION OF AN ARTERIOVENOUS MALFORMATION, ROTATABLE IMAGING SYSTEM AND COMBINATION OF A ROTATABLE IMAGING SYSTEM AND AN IRRADIATION UNIT

CROSS REFERENCE TO RELATED APPLICATIONS

This application claims priority of German application No. 10 2011 076 855.6 filed Jun. 1, 2011, which is incorporated by reference herein in its entirety.

FIELD OF INVENTION

The invention relates to a method for the functional visualization and localization of an arteriovenous malformation (AVM) with the aid of an X-ray tomographic examination by means of a rotatable imaging system. Furthermore, the invention also relates to a rotatable imaging system and a combination of rotatable imaging system and to an irradiation unit for performing the method according to the invention.

BACKGROUND OF INVENTION

Arteriovenous malformations (AVMs) are direct vascular connections between arteries and veins without an intermediate capillary bed. This is a disorder in which the arterial, i.e. oxygen-rich, blood flows out of an artery and drains directly into a vein without the oxygen contained therein being taken up by the tissue. Depending on the size of the AVM, a not inconsiderable volume of blood can be transferred. Whether clinical significance attaches to such a malformation is dependent on the site at which it is located and its size.

Irradiating the site with ionizing radiation, in a similar manner to treatment of a tumor, is used as a method of treating such arteriovenous malformations. The objective in this case is to direct the radiation at the nidus—i.e. the aggregation of vessels between artery and vein—ideally on the arterial inflow side or alternatively on the venous outflow side, wherein it is intended that the other side in each case should receive the minimum possible dose, i.e. should suffer as little damage as possible. Toward that end it is necessary on the one hand to identify the precise location of the nidus and on the other hand also to establish the arterial and venous assignment of the vessels belonging to the nidus.

For optimum localization of the AVM it is usual to carry out a 3D rotation angiography with the aid of a rotatable imaging system, in particular a rotatable imaging system that is embodied for producing a CBCT (cone-beam computed tomography) image, in particular a C-arm system for producing a CBCT image, wherein a multiplicity of projections are recorded from a projection angle range of 180°+fan angle during a contrast agent injection and a three-dimensional image of the vessels filled with contrast agent is recorded in the region of the AVM. In order to assign the feeder and/or draining vessels, a time series comprising projective 2D X-ray photographs is generated in most cases during the uptake of contrast agent with the aid of which the feeder and draining vessels are to be identified. The patient is exposed to an additional dose for this purpose.

SUMMARY OF INVENTION

It is therefore the object of the invention to discover a method by means of which it is possible with confidence to classify the AVM vessels into feeder and/or draining vessels, without causing an additional dose exposure.

This object is achieved by means of the features of the independent claims. Advantageous developments of the invention are the subject matter of subordinate claims.

The inventor has recognized that it is possible within the scope of a 3D rotation angiography examination, for example by means of a rotatable imaging system, in particular a rotatable imaging system embodied for producing a CBCT (cone-beam computed tomography) image, in particular a C-arm system for producing a CBCT image, to detect arteriovenous malformations with simultaneous flooding with contrast agent and at the same time, by subdividing the total number of projections acquired over the uptake time through intelligent division into at least three, preferably three to six, in each case cohesive projection ranges, to reconstruct a corresponding number of tomosynthesis image datasets succeeding one another in time with the aid of a digital tomosynthesis method, which image datasets enable the flow of the contrast agent to be determined and consequently permit the vessels in the located nidus to be assigned to the arterial and/or venous side. Furthermore, these tomosynthesis image datasets acquired in this way enable a precise localization of the now classified vessels of the nidus, such that—preferably immediately and without transfer of the patient between different imaging systems and therapy systems in the meantime—a spatially extremely precise irradiation of the nidus can be carried out with the aid of a therapeutic irradiation unit coupled in a defined manner to the reference system of the imaging system. In this case the irradiation planning takes place immediately after the detection of the nidus by means of the imaging system with subsequent irradiation, without the patient being transferred. Positioning errors can largely be avoided as a result.

It is pointed out that position corrections by means of the patient table of the irradiation system nevertheless continue to remain possible, since in this case the system has knowledge of such corrections of the patient table and can take these into account accordingly.

The inventor accordingly proposes a method for the functional visualization and localization of an arteriovenous malformation (AVM) with the aid of an X-ray tomographic examination by means of a rotatable imaging system for producing tomographic images, said method comprising the following steps of:

scanning a patient in an examination region containing at least one AVM and generating a multiplicity of projections at different projection angles over a predetermined projection angle range during the contrast agent uptake time, using the projections by subdividing the multiplicity of projections over the predetermined projection angle range into at least three partial projection datasets consisting of cohesive partial projection angle ranges, wherein the projections of each partial projection dataset belong in each case to different consecutive time windows of the total duration of the scan, and calculating a time series of tomosynthesis image datasets with the aid of a digital tomosynthesis method, and determining the vessels flooded by contrast agent in each of the time windows from the tomosynthesis image datasets, wherein vessels flooded first are assigned to arterial and vessels flooded last to venous vessels.

The projections hitherto used only in partial projection datasets can advantageously be used again in their totality in order to arrive at an improved tomographic visualization by reconstruction of the examination region with the aid of all of the projections over the entire projection angle range and thereby enable the at least one AVM to be spatially visualized and localized particularly easily.

A time series containing overlaid image datasets from the time-independent tomographic visualization and the time-dependent tomosynthesis image datasets can advantageously be output, as a result of which the present flow of the contrast agent can be particularly well visualized.

It is furthermore favorable if the partial projection angle ranges are set in such a way that except for +/−1 projection dataset each of the partial projection datasets has the same number of projections. This enables a consistent image quality to be achieved over the total number of tomographic datasets produced.

The predetermined projection angle range can be subdivided particularly favorably into three partial projection angle ranges, each covering 40° to 70°.

In order to highlight the contrast agent more vividly, the tomosynthesis image datasets can be subjected to threshold value filtering prior to the overlaying of the image datasets.

Furthermore, grayscale values of the tomosynthesis image datasets can be replaced by time-window-specific pseudocolors for the overlaying of the image datasets.

It is also advantageous to perform the reconstruction of the additional tomographic visualization of the examination region from the totality of projections over the entire scanned projection angle range by means of a filtered back projection (FBP).

Finally, an irradiation plan can be produced in such a way that a radiation dose is determined for occluding the patency of the AVM between arterial and venous side. It is advantageous in this case if an irradiation plan is produced on the basis of the tomographic visualization of the at least one AVM and the feeder and draining vessels of the at least one AVM are localized in such a way that the maximum radiation dose is applied in the AVM at that point where the smaller number of inflows to and/or outflows from the AVM are present. Equally, it can also be taken into account in the irradiation planning that the patency of the AVM between arterial and venous side is occluded using an absolute minimum radiation dose. What is achieved overall by means of said measures is that ultimately the total exposure of the patient to radiation is minimized.

In addition to the above-described method according to the invention, the inventor also proposes a rotatable imaging system, in particular a rotatable imaging system embodied for producing a CBCT (cone-beam computed tomography) image, in particular a C-arm system for producing a CBCT image, comprising a rotatable emitter-detector system having an X-ray tube for emitting a cone beam and an oppositely disposed flat-panel detector and a computer which is connected thereto and has a program memory in which is stored at least one program which during operation performs the above-described method according to the invention with the exception of the radiotherapeutic aspects.

Also proposed is a combination of a rotatable imaging system, in particular a rotatable imaging system embodied for producing a CBCT (cone-beam computed tomography) image, in particular a C-arm system for producing a CBCT image, and a therapeutic irradiation unit, comprising:

an emitter-detector system which is rotatable through at least 180° and has an X-ray tube for emitting a cone beam, and an oppositely disposed flat-panel detector, an irradiation unit having a controllable therapeutic radiation source, and a computer which has a program memory in which is stored at least one program which during operation performs the above-described method according to the invention with the radiotherapeutic aspects.

BRIEF DESCRIPTION OF THE DRAWINGS

The invention is described in more detail below with reference to the figures, with only the features necessary to an understanding of the invention being shown. The following reference signs are used: 1: C-arm system; 2: X-ray tube; 3: flat-panel detector; 4: C-arm; 5: housing; 6: table; 7: patient; 8: computer; 9: radiation source; 10: therapeutic irradiation unit; A: artery; AVM: arteriovenous malformation; G: vessel; N: nidus; ($Prg_1$-$Prg_n$): computer program; V: vein.

In the figures:

FIG. 4: is a schematic representation of the AVM from FIG. 3 showing isodose lines of the radiation treatment.

DETAILED DESCRIPTION OF INVENTION

Figure 1:
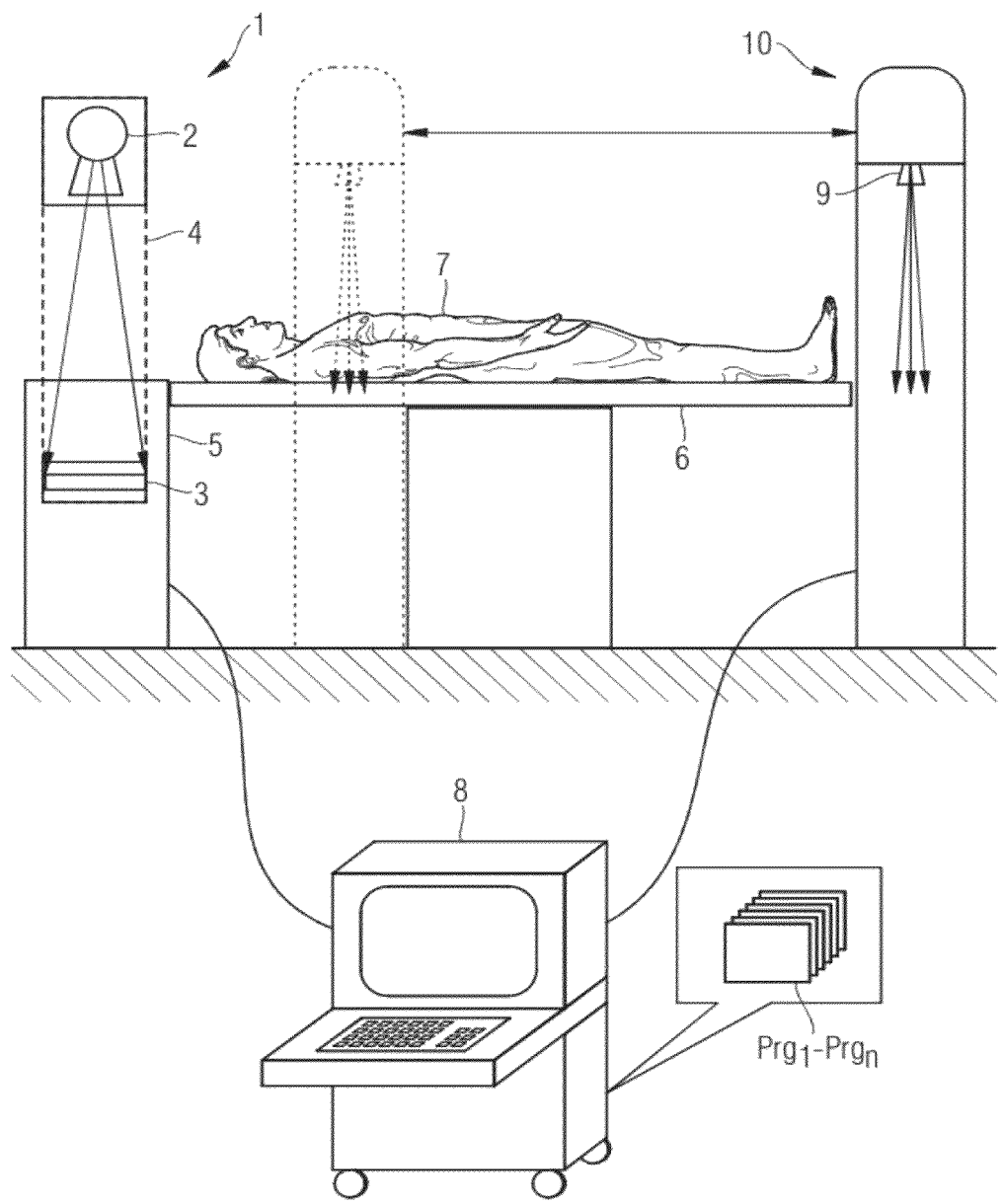
FIG. 1: shows a combination of C-arm system and therapeutic irradiation unit.

FIG. 1 shows schematically on the left-hand side a C-arm system 1 having an X-ray tube 2 and an oppositely disposed flat-panel detector 3. The X-ray tube 2 and the flat-panel detector 3 are mounted at the ends of a C-arm 4, the latter being capable of being pivoted circularly around the table 6 with the aid of a movement mechanism arranged on the housing 5 and not shown in further detail and in the process scanning the patient 7 positioned on the table 6. For the purpose of the scan the table 6 is moved into the scanning field of view of the C-arm 4.

The C-arm 4 is controlled by way of a computer 8 which also has a memory in which are stored computer programs $Prg_1$-$Prg_n$ which during operation also perform the methods according to the invention. Accordingly, a multiplicity of projections are recorded during the rotatory scanning of the patient 7, and a tomographic image of the examination region of the patient is reconstructed with the aid of all of the projections on the one hand and on the other hand the total number of projections is subdivided into at least three partial ranges relating to progressive time periods and these are in each case reconstructed with the aid of a digital tomosynthesis method. At the same time contrast agent is taken up in the blood vessels of the scanned region during the scanning, such that the thus obtained time series comprising tomosynthesis image datasets represents the takeup of the contrast agent. On the basis of the acquired tomographic images it is now possible on the one hand to detect and localize an arteriovenous malformation (AVM) that may be present and on the other hand to determine on the basis of the progression of the contrast agent over time in the vessels of the AVM—which in most cases form a nidus, i.e. an agglomeration of fine blood vessels,—which of the blood vessels possess an arterial or, as the case may be, venous character.

A region that is to be ablated can now be identified on the basis of the tomographic data, through which region the flow through the AVM can be prevented with minimum possible damage to surrounding regions. If a form of radiation treatment using ionizing radiation is employed for this, this can be applied by means of the therapeutic irradiation unit 10 with the adjustable radiation source 9 likewise shown in FIG. 1.

Since said irradiation unit 10 is coupled in a defined manner to the movable patient table 6, it is not necessary to reposition or relocate the patient 7 between localization of the AVM and irradiation, so the irradiation can be performed with pinpoint precision. In this case the irradiation planning and the control of the irradiation unit 10 can again be accomplished by means of the computer 8, thus making it unnecessary for any complex exchange of data to take place between different computing systems.

Figure 2:
FIG. 2: shows an arteriovenous malformation (AVM) in a projective X-ray photograph.

FIG. 2 shows a projective image of an AVM in order to illustrate the problem of AVM localization and treatment planning. It is revealed here that without spatial visualization it is very difficult to differentiate the arterial and venous vascular regions and to localize where an optimal ablation— i.e. covering the smallest possible area—should be applied in order to prevent the arteriovenous connection by way of the AVM.

Figure 3:
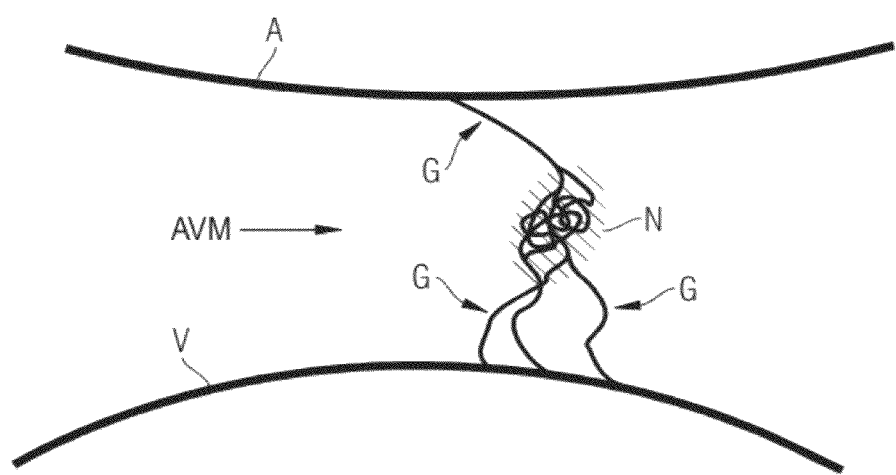
FIG. 3: is a schematic representation of an AVM with nidus.

FIG. 3 is a highly schematic representation showing such an AVM, consisting of a multiplicity of vessels G constituting an undesirable connection between a large arterial blood vessel A and a large venous blood vessel V. The hatched area is intended in this case to identify the region of the nidus N, which is to say a region in which the vessels G aggregate, forming a knotted tangle of vessels or a kind of nest (=nidus).

When such an AVM is localized, the arterial and/or venous assignment of the individual vessels G can be determined with the aid of the above-described method and consequently an optimally small region identified for tissue ablation by means of irradiation.

FIG. 4 shows such a region marked by the isodose lines indicated for 90%, 80% and 70% of the local maximum dose that is to be applied. As can be seen from FIG. 4, this region lies in the vicinity of the only connection of the nidus to the artery, which means that only a small volume must be ablated in order to prevent the harmful blood flow between artery A and vein V.

All in all, therefore, a method, rotatable imaging system and combination of imaging system and irradiation unit for the functional visualization and localization of an AVM are disclosed by means of the present invention, wherein:

a patient is scanned over a predetermined projection angle range during the time for contrast agent to be taken up, a reconstruction of the examination region is carried out using all projections over the entire projection angle range and the at least one AVM is localized, the multiplicity of projections is subdivided into at least three partial projection datasets, the projections of each partial projection dataset in each case belonging to different consecutive time windows of the total duration of the scan, a time series comprising tomosynthesis image datasets is generated by means of the partial projection datasets, and an arterial and/or venous assignment of the vessels flooded with contrast agent takes place on the basis of the time series of tomosynthesis mage datasets.

Although the invention has been illustrated and described in detail on the basis of the preferred exemplary embodiment, it is not limited by the disclosed examples and other variations can be derived therefrom by the person skilled in the art without departing from the scope of protection of the invention.

The invention claimed is:

1. A method for functional visualization and localization of an arteriovenous malformation with an X-ray tomographic examination by a rotatable imaging system, comprising:

scanning a patient in an examination region containing the arteriovenous malformation by the rotatable imaging system;

generating a plurality of projections at different projection angles over a predetermined projection angle range during a contrast agent uptake time;

subdividing the plurality of projections into at least three partial projection datasets comprising cohesive partial projection angle ranges, wherein projections in each partial projection dataset belong to different consecutive time windows during the scan;

reconstructing a time series of tomosynthesis image datasets each from the projections in each partial projection dataset using a digital tomosynthesis method;

determining vessels flooded by the contrast agent in each of the different consecutive time windows from the time series of the tomosynthesis image datasets;

assigning the vessels flooded first to arterial vessels and the vessels flooded last to venous vessels;

localizing the arteriovenous malformation based on the assigning of progression of the contrast agent over time in the vessels; and marking a region lies in a vicinity of an only connection of a nidus to the arterial vessels based on the localization of the arteriovenous malformation in which a treatment is applied for occluding a patency of the arteriovenous malformation between the arterial vessels and the venous vessels.

2. The method as claimed in claim 1, further comprising reconstructing the examination region with all of the projections over the entire projection angle range to provide a spatial visualization and localization of the arteriovenous malformation.

3. The method as claimed in claim 2, wherein the reconstruction of the examination region with all of the projections is performed by a filtered back projection.

4. The method as claimed in claim 1, wherein a time series of overlaid image datasets is outputted by overlaying time-independent tomographic visualization with time-dependent tomosynthesis image datasets.

5. The method as claimed in claim 4, wherein the tomosynthesis image datasets are filtered by a threshold value prior to the overlaying for visualizing the contrast agent exclusively.

6. The method as claimed in claim 4, wherein grayscale values of the tomosynthesis image datasets are replaced by time-window-specific pseudocolors for the overlaying.

7. The method as claimed in claim 1, wherein the partial projection angle ranges are set in such a way that each of the partial projection datasets has a same number of projections.

8. The method as claimed in claim 1, wherein the predetermined projection angle range is subdivided into three partial projection angle ranges.

9. The method as claimed in claim 8, wherein each of the three partial projection angle ranges covers 40° to 70°.

10. The method as claimed in claim 1, wherein an irradiation plan is produced using the time series of the tomosynthesis image datasets, and wherein a feeder vessel and a draining vessel of the arteriovenous malformation are localized such that a radiation dose is determined for occluding a patency of the arteriovenous malformation between the arterial vessels and the venous vessels.

11. The method as claimed in claim 10, wherein a total exposure of the patient to the treatment for the patency of the arteriovenous malformation is minimized.

12. The method as claimed in claim 1, wherein a maximum treatment is applied to the arteriovenous malformation at the region.

13. The method as claimed in claim 1, wherein the rotatable imaging system is a C-arm system.

14. The method as claimed in claim 13, wherein the predetermined projection angle range is set between 180° and a maximum movement range of the C-arm system.

15. An imaging system, comprising:
- a rotatable emitter-detector system having an X-ray tube for emitting a cone beam and an oppositely disposed flat-panel detector; and
- a computer for performing a method as claimed in claim 1.

16. A system having a rotatable imaging system and a therapeutic irradiation unit, comprising:
- an X-ray tube connected to the rotatable imaging system for emitting a cone beam;
- an oppositely disposed flat-panel detector connected to the rotatable imaging system for producing tomographic images, wherein the rotatable imaging system is rotatable through at least 180°;
- an irradiation unit having a controllable therapeutic radiation source; and
- a computer for performing a method as claimed in claim 1.

* * * * *